United States Patent [19]
Gerow

[11] 3,991,752
[45] Nov. 16, 1976

[54] PENILE IMPLANT
[75] Inventor: Frank J. Gerow, Houston, Tex.
[73] Assignee: Dow Corning Corporation, Midland, Mich.
[22] Filed: Dec. 4, 1975
[21] Appl. No.: 637,557

[52] U.S. Cl. ................................................ 128/79
[51] Int. Cl.² ......................................... A61F 5/00
[58] Field of Search ...................... 128/79, 305; 3/1

[56] References Cited
UNITED STATES PATENTS

| | | | |
|---|---|---|---|
| 3,832,996 | 9/1974 | Kalnberz | 128/79 |
| 3,853,122 | 12/1974 | Strauch et al. | 128/79 |
| 3,893,456 | 7/1975 | Small et al. | 128/79 |
| 3,954,102 | 5/1976 | Buuck | 128/79 |

Primary Examiner—Lawrence W. Trapp
Attorney, Agent, or Firm—Howard W. Hermann

[57] ABSTRACT

A penile implant formed of a soft silicone rubber having a bulbous distal end which tapers to the proximal end and has a longitudinal groove formed on the ventral side which notches the proximal end.

6 Claims, 4 Drawing Figures

PENILE IMPLANT

BACKGROUND OF THE INVENTION

The more liberal attitude towards sexually related problems in the western world has been one reason for the increased public interest in the subject of sexual impotency.

Impotency is a lack of copulative power. Potency is dependent on the following factors:
1. Libido
2. Erection
3. Ejaculation
4. Orgasm The mechanism of coitus starts with libido and erection and terminates with ejaculation and orgasm. There are three types of impotency in the human male: the first being erectile, the second, ejaculatory; and the third, premature ejaculatory. The causes which bring about impotency are broadly speaking functional or organic or a combination of the two. In fact, organic causes are almost always accompanied by functional causes since the mechanism of erection and the mechanism of ejaculation are mediated via a complex group of peripherally and centrally controlled reflexes. The least trauma to the nerves supplying the muscles involved in erection or ejaculation may result in non-effectual function.

Organic causes include local pathologic conditions of the male genitalia, acute and systemic diseases such as chronic alcoholism or anemia and diseases of the nervous system such as diseases of the brain and spinal cord. Functional causes include many different types of psychoneuroses.

One of the types of male impotency that has been successfully helped by surgical management is erective impotency. Erective impotency is the persistant inability to obtain or maintain a penile erection sufficient to allow orgasm and satisfactory ejaculation during heterosexual coitus. Erective impotency may have organic causes such as diabetes or functional causes such as psychoneurosis.

The justification of a surgical approach to the correction of psychological impotency lies in the problems related to the psychotherapeutic treatment of the patient with absolute impotency with one or more years duration. The patient who consults a psychiatrist for treatment presents the highest failure rate; if the patient achieves some degree of success after prolonged psychotherapy, he is likely to revert to his impotent state with the usual social and business stresses and, of course, with his first failure to achieve an erection, will tend to fail again. Impotency, in many of these cases, is such an overriding symptom that the necessity of curing the symptom (i.e., the impotency) is necessary before the underlying psychoneurosis can be reached. There seems to be a general feeling that if the impotency can be corrected, many of the psychoneurotic manifestations, which are a function of transference after the patient discovers he is impotent, would be self resolving. Surgical correction of the impotency will allow the therapist greater success with the psychoneurotic problems that cause the impotence.

For many years, external rubber or plastic dildos have been used to either provide or support an erection. The short comings of such external prosthesis are discomfort and the lack of penile skin contact with the vaginal mucosa. The first successful penile reconstruction, by Sir Harold Gillies, in 1957, utilized a cartilage graft brace. An unsuccessful use of an acrylic rod, as a brace, was made by Goodwin and Scott in the early 1950's. The use of cartilage or bone as an implant is not satisfactory because the materials are absorbed either in part or totally. The idea of an os penis led Loeffler, Sayegh, and Lash, in 1964, to implant an acrylic rod between the corpora cavernosa. G. E. Beheri, in 1966, disclosed the use of polyethylene rods implanted into the center of each of the corpora cavernosa as an aid to overcoming impotency. A t-shaped prosthesis has been fitted between the corpora cavernosa with a crossbar butted against the pubic bone. The patent to Kalnberz, U.S. Pat. No. 3,832,996, issued Sept. 3, 1974, discloses an endo-prosthesis for the penis which is yoke-like in configuration having a portion of the arms immersed in the cavernous bodies near the glans. In the paperback book entitled *Self-Image Surgery* by Maxine Mesinger at page 142, there is a perspective drawing of a penile implant which resembles in some respects the inventor's implant. This disclosed implant, however, has a shoulder located approximately one-third back from the dorsal end. Furthermore, both the dorsal and proximal ends are notched. Also, the upper surface of the implant is arced while that of the inventor's is planar throughout.

SUMMARY OF THE PRESENT INVENTION

This invention is directed at a penile implant substantially oval in configuration having a longitudinal groove or channel formed on its ventral side and being significantly tapered from its distal end to its proximal end. The volume of the distal end is 100 percent greater than the proximal end. Both the distal and proximal ends are blunted. Because of the blunting of the distal end it tends not to erode through tissue overlying the urethra or the glans penis as was the case in many prior art devices during normal movement or during coitus. When implanted the channel in the prosthesis sits astride the sectioned intercorporal septum on which it rides. The comparative bluntness of the distal end reduces the pressure per square inch on that surface and thereby reduces the possibility of erosion as mentioned. The implant is designed to significantly reduce the amount of tension per square inch in the areas where the greatest possibility for tension exists once the device is implanted.

The tapering design provides an implant that assures that the usual contractures of the tissues around the implant will tend to keep it out in the penile shaft. Furthermore, the width of the distal end prevents the prosthesis from moving back into the narrow pocket provided for the proximal end. This design prevents the implant from riding back under the symphysis pubis into one of the crurae, a common fault in many prior art penile implants.

Due to its construction and the soft material from which it is formed the implant is quite flexible and this provides internal "hinging" or a moving interface effect with the surrounding penile tissue.

The implant is formed from the same soft material throughout rather than different materials as is found in some prior art devices.

BRIEF DESCRIPTION OF THE DRAWINGS

Other intended advantages of the present invention will become obvious to those skilled in the art from a reading of the following detailed description when read in conjunction with the accompanying drawings wherein.

DESCRIPTION OF PREFERRED EMBODIMENTS

Figure 1:
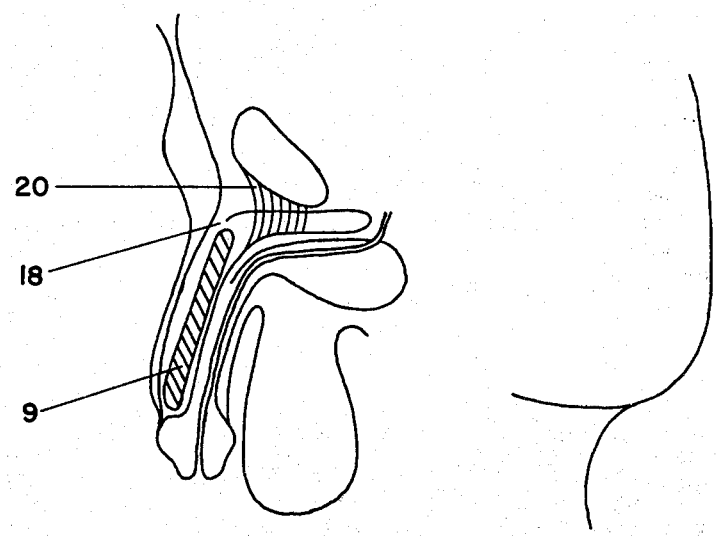
FIG. 1 is a side elevational view partly in section of the endo-prosthesis in accordance with the invention after implantation in the penis.
Figure 2:
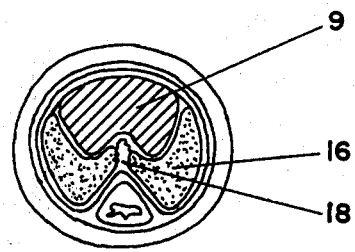
FIG. 2 is a section taken at right angles to the axis of the penis on lines 2—2 of FIG. 3.
Figure 3:
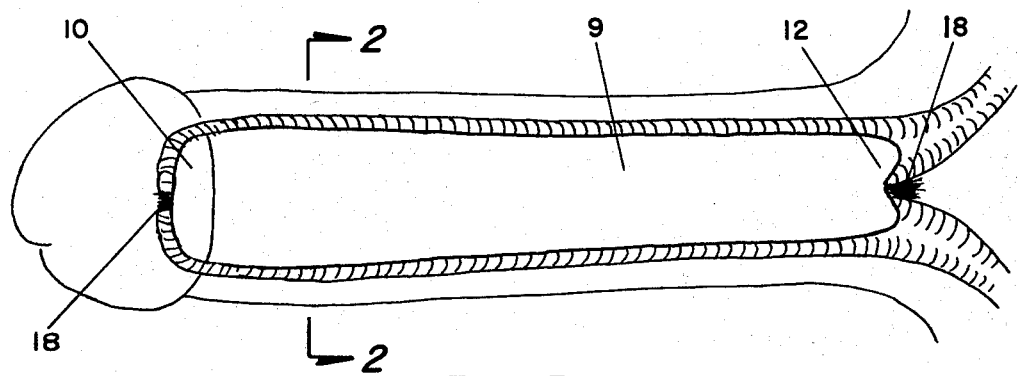
FIG. 3 is a top plan view of the endo-prosthesis shown in FIG. 1.
Figure 4:
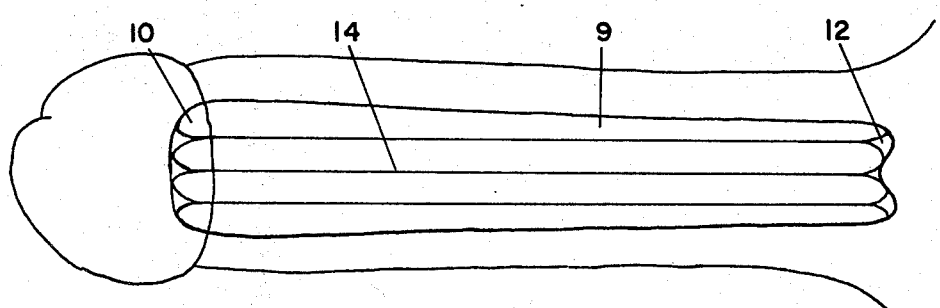
FIG. 4 is a bottom plan view of the endoprosthesis shown in FIG. 1.

The penile implant 9 shown in the drawings can be formed from any moldable, very soft, pliable material such as a non-toxic, thermoplastic material or vulcanizable material although silicone rubber is preferred by the inventor.

By very soft silicone rubber, the inventor means either an RTV (room temperature vulcanized) silicone rubber which is an organopolysiloxane composition curable at room temperature or a heat vulcanizable silicone rubber which includes a base polymer such as dimethylsiloxane, a cross linking agent such as dichlorobenzylperoxide and reinforcing silicone fillers. Silicone rubbers, for the most part, are heat stable, will not adhere to other materials except certain silicones and are substantially physiologically inert in the animal body.

The implant itself is soft, solid and somewhat oval in configuration tapering without interruption from the distal portion 10 to the proximal portion 12. The upper surface of the implant is planar throughout its length. The ventral surface of the implant has a deep longitudinal groove or channel 14 formed therein extending from a plane short of the distal portion 10 to the proximal portion 12 notching the proximal portion 12. Care was taken to prevent the distal portion 10 from being notched. The edges of the distal portion 10 and the proximal portion 12 are arced or blunted to prevent erosion through tissue which overlies the urethra and permitting a sliding of the implant in the tissues without injury thereto.

The implantation of the endo-prosthesis is done through a lateral approach avoiding any trauma to the nerves and vessels. The proximal corpora is entered; the dissection is carried across the base of the mobile penis, across the intercorporal septum and into the distal corpora 16 on the left side. It is carried down the shaft of the penis by sharp and blunt dissection immediately deep to the corporal capsule, thereby minimizing injury to the vasculature of the corpora cavernosa. The dissection is carried down to the area immediately behind the proximal edge of the glans. An expander is used in this pocket to achieve further expansion of the pocket by bluntly spreading the tissue. In area of the suspensory ligament 20, the intercorporal septum 18 becomes quite dense. One of the mechanisms for erection is that the suspensory ligament pulls on the base of the penile shaft which has become congested. As this congestion continues the ligament has a tourniquet effect aiding the penile shaft in maintaining its erection. The dissection cuts the septum loose for the length of the implant while leaving the septum attached dorsally and proximally. The proximal attachment is forward of the suspensory ligament and its area of contiguousness with the septum. The prosthesis is inserted (literally popped into place) and positioned so that the groove straddles the intercorporal septum 18. The distal portion 10 of the implant is positioned in a slightly spaced relationship to the connected portion of the septum 18 proximate the glans penis. The proximal portion 12 of the implant is positioned slightly forward of the connected portion of the septum 18 in its area of contiguousness with the suspensory ligament 20. The dissected septum is stretched by the implant which in effect is in a sling provided by the septum when the penis is hanging straight down. When the penis with the implant is raised toward a right angle to the axis of the human body a sliding effect occurs. The dorsal tissue will move distally as will the surface of the implant. The Shore A durometer of the material of the implant is in the range of from 25–50 although typically it is 30. The prosthesis is inserted and placed so that the groove straddles the intercorporal septum 18. The corporal incision is closed in the usual manner and a gentle compression dressing to be changed every two or three days is placed around the penis. The patient is instructed to abstain completely from sexual intercourse for at least 6 weeks and between 6 months to a year after surgery the patient begins having an erection, if the cause of impotence is only psychological, around the prosthesis; this presents no problem since by that time the capsule is really well formed.

A variation of the implant disclosed herein can be constructed by forming the two sides of the implant from the distal portion 10 to the proximal portion 12 as envelopes which can be filled with physiologically compatible fluids such as saline or silicone fluids to a consistency which in effect could be tailored to whatever softness the surgeon may desire.

Various modifications and variations of the invention as described herein will become obvious to those skilled in the art from a reading of the foregoing. It is to be understood, therefore, that within the scope of the appended claims the invention may be practiced otherwise than as specifically described.

That which is claimed is:

1. A prosthesis for the penis comprising a generally oval shank portion having a distal portion at one end and a proximal portion at the other end, the distal portion and the proximal portion each having a face with arced surface, the prosthesis tapering from the distal portion to the proximal portion and having ventral surface, the ventral surface having a longitudinal channel formed therein extending through the face of the proximal portion notching it.

2. A prosthesis as set forth in claim 1 wherein the volume of the distal portion is fifty percent greater than the proximal portion.

3. A prosthesis as set forth in claim 1 wherein the shank portion has an upper surface, the upper surface being substantially planar.

4. A prosthesis as set forth in claim 1 wherein the prosthesis is formed of a soft elastomer.

5. A prosthesis as set forth in claim 4 wherein the elastomer is silicone rubber.

6. A prosthesis as set forth in claim 1 wherein the shank portion has sides, each side formed as an envelope, the envelope filled with a yieldable material.

* * * * *